United States Patent
Rappel

(10) Patent No.: US 9,330,477 B2
(45) Date of Patent: May 3, 2016

(54) SURGICAL STEREO VISION SYSTEMS AND METHODS FOR MICROSURGERY

(71) Applicant: DIGITAL SURGICALS PTE. LTD., Singapore (SG)

(72) Inventor: James K. Rappel, Singapore (SG)

(73) Assignee: Digital Surgicals PTE. LTD., Singapore (SG)

( * ) Notice: Subject to any disclaimer, the term of this patent is extended or adjusted under 35 U.S.C. 154(b) by 355 days.

(21) Appl. No.: 13/622,820

(22) Filed: Sep. 19, 2012

(65) Prior Publication Data

US 2013/0076863 A1    Mar. 28, 2013

Related U.S. Application Data

(60) Provisional application No. 61/537,592, filed on Sep. 22, 2011.

(51) Int. Cl.
*H04N 13/00* (2006.01)
*G06T 11/00* (2006.01)
*G02B 21/22* (2006.01)

(52) U.S. Cl.
CPC ............... *G06T 11/00* (2013.01); *G02B 21/22* (2013.01); *H04N 13/004* (2013.01); *G06T 2210/41* (2013.01)

(58) Field of Classification Search
None
See application file for complete search history.

(56) References Cited

U.S. PATENT DOCUMENTS

| | | |
|---|---|---|
| 5,749,362 A | 5/1998 | Funda et al. |
| 6,396,627 B1 | 5/2002 | Tachihara et al. |
| 6,429,418 B1 | 8/2002 | Chahl et al. |
| 6,522,310 B1 | 2/2003 | Kim |
| 6,926,409 B2 | 8/2005 | Togino et al. |
| 6,927,905 B1 | 8/2005 | Kashitani et al. |
| 7,180,663 B2 | 2/2007 | Collender et al. |
| 2002/0120424 A1* | 8/2002 | Hauger et al. ............... 702/150 |
| 2003/0071893 A1 | 4/2003 | Miller et al. |
| 2003/0142203 A1 | 7/2003 | Kawakami et al. |

(Continued)

FOREIGN PATENT DOCUMENTS

| | | |
|---|---|---|
| EP | 0672389 B1 | 8/1998 |
| WO | WO9514252 A1 | 5/1995 |

(Continued)

OTHER PUBLICATIONS

Schwald, B. et al., "Implementation and Evaluation of an Augmented Reality System Supporting Minimal Invasive Interventions", AMI-ARCS, Rennes, France, Sep. 30, 2004, pp. 41-48 A.

*Primary Examiner* — Jay Patel
*Assistant Examiner* — Reza Aghevli
(74) *Attorney, Agent, or Firm* — Clements Bernard PLLC; Lawrence A. Baratta, Jr.; Christopher L. Bernard

(57) ABSTRACT

Surgical stereo vision systems and methods for microsurgery are described that enable hand-eye collocation, high resolution, and a large field of view. A digital stereo microscope apparatus, an operating system with a digital stereo microscope, and a method are described using a display unit located over an area of interest such that a human operator places hands, tools, or a combination thereof in the area of interest and views a magnified and augmented live stereo view of the area interest with eyes of the human operator substantially collocated with the hands of the human operator.

19 Claims, 7 Drawing Sheets

(56) References Cited

U.S. PATENT DOCUMENTS

| | | |
|---|---|---|
| 2003/0174292 A1 | 9/2003 | White |
| 2004/0085517 A1 | 5/2004 | Togino et al. |
| 2004/0125447 A1 | 7/2004 | Sato et al. |
| 2004/0155956 A1 | 8/2004 | Libbey |
| 2004/0196438 A1 | 10/2004 | Togino |
| 2004/0220464 A1 | 11/2004 | Benninger et al. |
| 2005/0030489 A1 | 2/2005 | Togino |
| 2005/0117118 A1 | 6/2005 | Miller et al. |
| 2005/0180019 A1 | 8/2005 | Cho et al. |
| 2005/0248972 A1 | 11/2005 | Kondo et al. |
| 2006/0181607 A1 | 8/2006 | McNelley et al. |
| 2007/0035493 A1 | 2/2007 | Chang |
| 2007/0058035 A9 | 3/2007 | Fujie et al. |
| 2007/0121202 A1 | 5/2007 | Riederer |
| 2007/0121203 A1 | 5/2007 | Riederer |
| 2007/0156017 A1* | 7/2007 | Lamprecht et al. ............ 600/102 |
| 2007/0236514 A1* | 10/2007 | Agusanto et al. ............. 345/646 |
| 2008/0055405 A1* | 3/2008 | Maddison ....................... 348/79 |
| 2008/0142597 A1 | 6/2008 | Joseph et al. |
| 2008/0194930 A1* | 8/2008 | Harris et al. .................. 600/310 |
| 2008/0239063 A1* | 10/2008 | Ishikawa et al. ................ 348/46 |
| 2009/0196526 A1* | 8/2009 | Schmid et al. ................ 382/278 |
| 2010/0013910 A1* | 1/2010 | Farr ............................... 348/51 |
| 2010/0103247 A1 | 4/2010 | Lim et al. |
| 2010/0141739 A1* | 6/2010 | Luber et al. .................... 348/46 |
| 2010/0149323 A1* | 6/2010 | Yoo et al. ........................ 348/66 |
| 2010/0160789 A1* | 6/2010 | Dilworth et al. .............. 600/476 |
| 2011/0032335 A1* | 2/2011 | Sander ............................ 348/46 |
| 2012/0002084 A1 | 1/2012 | Weissman et al. |

FOREIGN PATENT DOCUMENTS

| | | |
|---|---|---|
| WO | 2004/029786 A1 | 4/2004 |
| WO | WO2005109068 A1 | 11/2005 |
| WO | 2009/142443 A2 | 11/2009 |
| WO | WO2012105909 A1 | 8/2012 |

* cited by examiner

FIG. 1 *Prior Art*

SURGICAL STEREO VISION SYSTEMS AND METHODS FOR MICROSURGERY

CROSS-REFERENCE TO RELATED APPLICATION(S)

The present non-provisional patent application claims priority to U.S. Provisional Patent Application Ser. No. 61/537,592 filed Sep. 21, 2011 and entitled "A Surgical Stereo Vision System for Microsurgery," the contents of which are incorporated by reference herein.

FIELD OF THE INVENTION

Generally, the field of art of the present disclosure pertains to surgical vision systems and methods, and more particularly, to surgical stereo vision systems and methods for microsurgery that enable hand-eye collocation, high resolution, and a large field of view.

BACKGROUND OF THE INVENTION

Figure 1:
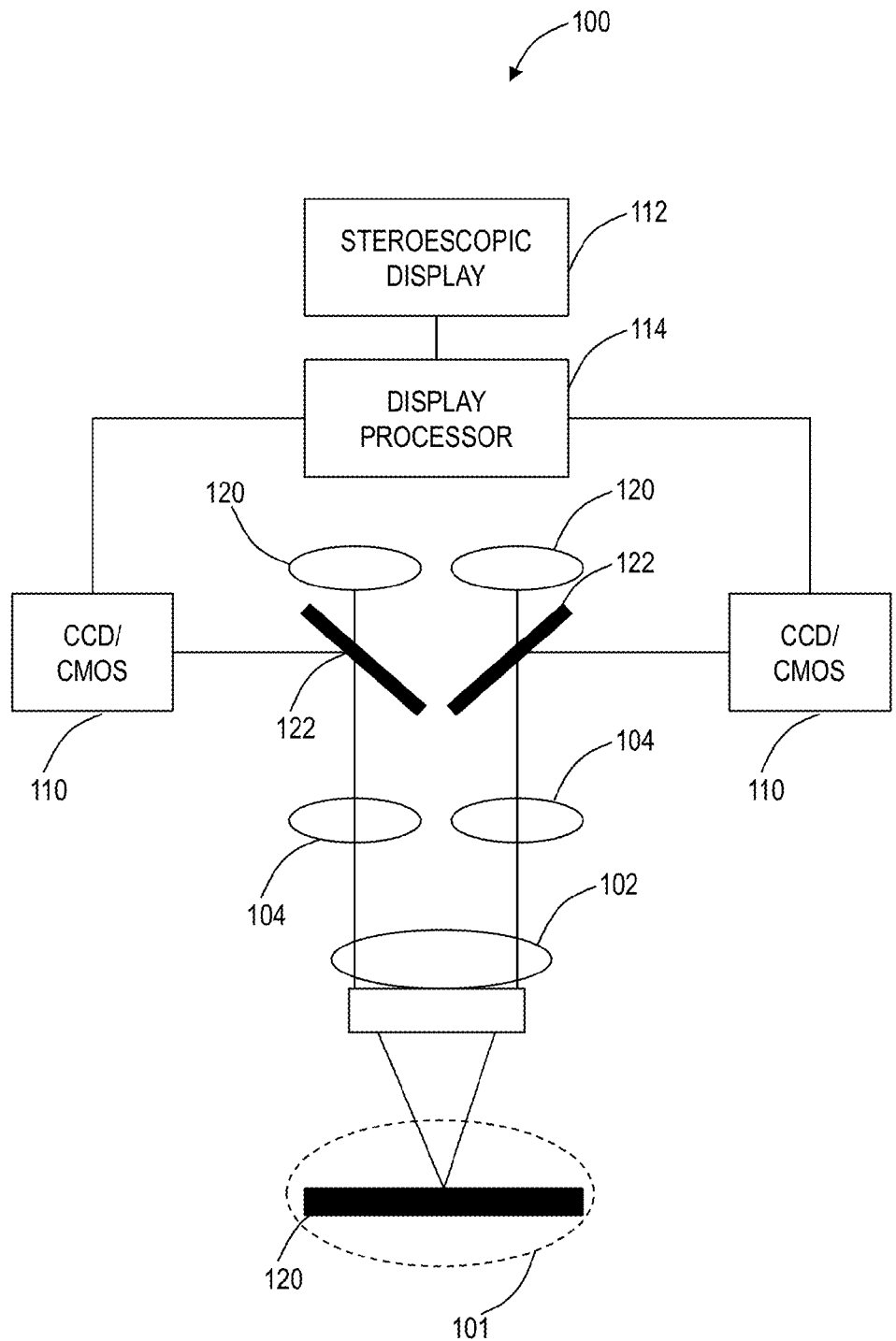

Micromanipulations such as microsurgery require a distortion free magnified and binocular stereoscopic view of its operating field 101. Surgical Loupes, Surgical Light Microscope (SLM) and its digital adaptation, namely, Digital Stereo Microscope (DSM) provide such views of the operating field 101. SLMs have a number of optical elements that provide magnification, working distance and distortion correction. SLMs have an objective lens for collecting the light from the subject, a pair of oculars for viewing the subject and a number of optical elements which enhances the view through magnification and correction of distortion. SLMs are improvements on the classical double barreled binocular microscope to address issues of distortion, limited working distance, limited field of view, and brightness. An exemplary prior art SLM/DSM 100 is illustrated in FIG. 1. To increase magnification, either an objective lens 102 is changed or zoom lens system 104 is moved. The pair of oculars provides views having the required parallax to the right and left eye. SLMs provide instant stereo view for depth perception to the human visual system. Operating fields 101 provided through visual aids such as SLMs, DSMs and surgical loupes should allow a user to perform bi-manual microsurgical manipulations with the subject/objects in the operating field and optionally sharing the operating field with one or more collaborators.

Figure 2:
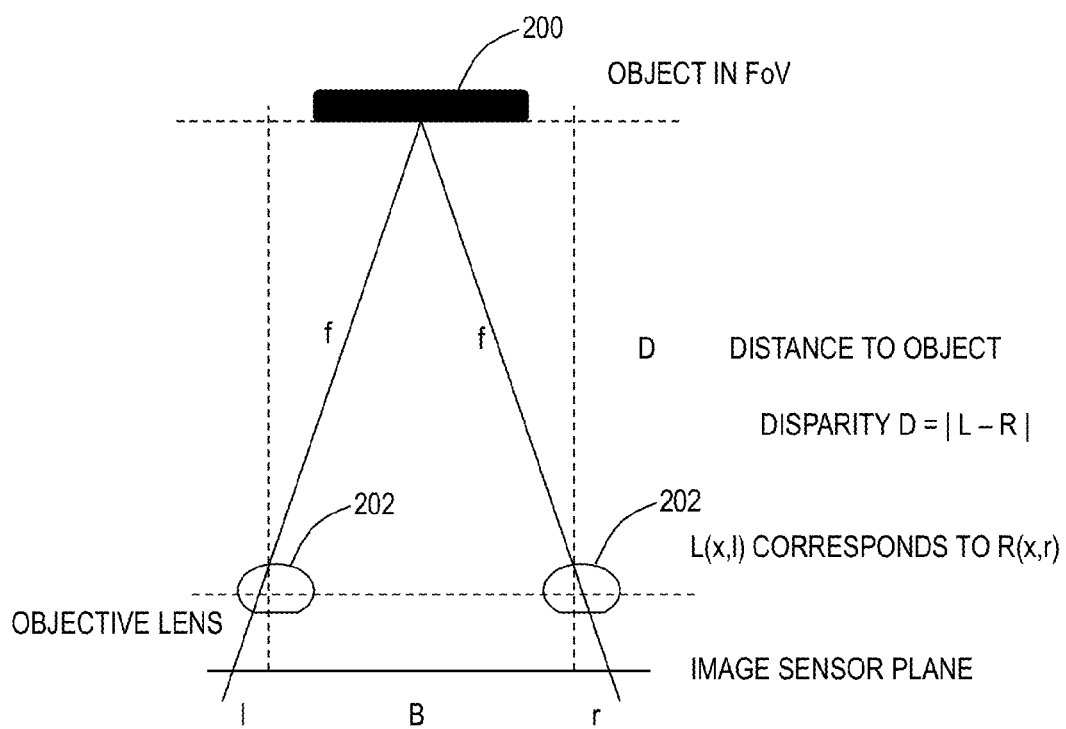

FIG. 2 illustrates the relationship between distance, D, to an object 200 from the lens 202, focal length, f, of the lens 202, separation, B, of the lenses 202 and the disparity |l−r| of the image pixels in the left and right eye views in a stereoscopic view. Field of View (FoV), Depth of Field (DoF), Working Distance (W) and magnification (Z) are inter-related in an optical system. When magnification is increased, the field of view and depth of field is decreased. Various conventional systems and methods have added optical elements to rectify these limitations but the key dependency between FoV and Z remains. Added optical elements also increase the size of the microscope, optical impedance and reduce the brightness. Additional lighting innovations further increase the size, but the main drawback of FoV and Z dependence still remains.

Using the current microscopes, it is not possible to view a location that is not in the optical path through the objective lenses 102 and the oculars 120. Users will need to reorient the object or subject (example, patient) to obtain a view from another angle. In addition, physical construction of the microscope allows very limited numbers of oculars. Optical microscopes do not allow additional content to be added to the view or enhance the view with mensuration or annotation.

Additionally, there are many usability issues in performing micro manipulations using SLMs. A user of a SLM gets visual fatigue because the exit pupil diameter of the ocular lens is very small and lateral movements of the observer causes motion in the field of view. Viewing stereo through surgical microscopes is also a learned skill. It takes significant amount of practice to be able to find the right combination of eye muscle coordination and inter-papillary distance setting of the microscope that allows viewing through both eye pieces at the same time to result in a brain-fusible stereo pair projected on to the retina. This makes stereoscopic viewing through binocular microscope tedious and tiring. Each time, when the eyes are taken away from the binocular eye pieces and brought back; there is a certain degree of eye muscle adjustment to be made before the view becomes stereoscopic. This inconvenience adds to the operational time and operator fatigue.

Another limitation is the narrow field of view. Microscope construction makes use of a large number of optical elements arranged in a barrel. The large number of optical elements narrows the field of view. FoV gets further reduced as the magnification is increased. Narrow field causes the surgeons to lose the visual context frequently. A typical corrective action is to zoom out to bring back the context and then zoom in to achieve magnification while maintaining the tool or tissue in the field of view. This too adds to the operational time and operator fatigue. Surgeons cooperate with human assistants who share the same workspace as the surgeon. The assistant should view what the surgeon is viewing, in order to be of operational assistance. Physical construction of SLM microscopes typically allow only up to one assistant. In addition, each surgeon should have independent control of viewing the same field-of-view by controlling the lighting, contrast and magnification.

Many surgeries last hours and the fixed posture (looking through the eye pieces) contributes significantly to the fatigue experienced by surgeons. In a lengthy surgery, multiple surgeons and assistants may time multiplex. Individual calibration of the microscope should be done to get continuity. Though magnified view is a significant surgical aid, due to the above limitations only very few surgeons are able to perform micro surgery, the surgery that uses microscopes, though there are far more surgeons with excellent surgical skills.

Referring back to FIG. 1, conventional SLMs/DSMs 100 use high resolution and speed imaging sensors such as (Charge Coupled Devices) CCDs 110 to supplement the oculars. The SLM/DSM 100 is retrofitted with imaging sensors at an eye piece 120 and then the view is sent to a stereoscopic monitor 112 via a display processor 114 to view the FoV of an object 120. Specifically, the CCDs 110 can receive the view from beam splitters 122 before the eye piece 120. Surgeon uses stereoscopic viewing techniques such as passive stereo glasses, active stereo shutter glasses and auto stereoscopic displays. Since the imagery is acquired and displayed digitally, these microscopes are called digital stereo microscopes (DSM). A commercial example is the digital stereo microscope by TrueVision™. When using the TrueVision™ microscope, surgeon can either look through binocular barrels of the optical microscope as in the case of the traditional microscope or look away at the stereoscopic screen to view the workspace. The disadvantages of the former approach have already been discussed. In the latter viewing setting, as the display 112 is located elsewhere, surgeon loses the key hand-eye collocation and as a result compromises the hand-eye coordination needed for highly dexterous manipulations under magnified view. In addition, since the basic field of view is captured using the objectives of a traditional SLM, it suffers many of the limitations of the SLM described earlier.

The human visual system has a variable resolution vision. The resolution drops from the foveal vision to the peripheral vision. The visual acuity deteriorates from central (−1, +1) degree visual field to the (−59, +110) degree visual field. Roughly, the (−2, +2) degree visual field has half the resolution of the (−1, +1) degree visual field, (−5, +5) degree visual field has half the resolution of the (−2, +2) visual field and (−12, +12) has half the resolution of the (−5, +5) visual field. However, SLMs or DSMs do not provide any visual aid to match the visual resolution variance. Performing such variable resolution without depth distortion effects is also a challenge.

Stereo microscopes without oculars are another conventional system. These use mirrors that rotate fast to project the right and left view to right and left eye without having an eye piece. A user of this microscope needs to place the users eyes aligned to the projected space to be able to see stereo. While the above system affords some freedom of head movement, the projected space is quite narrow and it is easy to slip out and loose stereo vision. This system also requires training to use and even after training, at each usage there is a task of aligning eyes to the projected space. Peripheral vision can easily distract the eyes from seeing stereo. These microscopes have not found a home in operating theatres yet and are used in the manufacturing industry for inspection of printed circuit boards and other miniature electronic assemblies.

BRIEF SUMMARY OF THE INVENTION

In an exemplary embodiment, a digital stereo microscope apparatus includes a display unit located over an area of interest such that a human operator places hands and/or tools in the area of interest and views a magnified and augmented live stereo view of the area interest with eyes of the human operator having a view substantially collocated with the hands and/or tools of the human operator; an image display located on a first side of the display unit providing the magnified and augmented live stereo view; an optical system and an image acquisition system located in part on a second side of the display unit providing image capture and data capture of the area of interest; and a processing system communicatively coupled to the image acquisition system and the image display providing the magnified and augmented live stereo view to the image display based on the image capture and the data capture of the area of interest from the optical system and the image acquisition system, wherein the optical system and the image acquisition system is configured to provide the image capture with adjustments to provide the magnified and augmented live stereo view performed by the processing system.

In another exemplary embodiment, an operating system with a digital stereo microscope includes an articulated arm comprising a display mounting system; a display unit connected to the display mounting system; an operating site over which the display unit is located such that a human operator places hands and/or tools in the operating site and views a magnified and augmented live stereo view of the operating site with eyes of the human operator having a view substantially collocated with the hands and/or tools of the human operator; an image display located on a first side of the display unit providing the magnified and augmented live stereo view; an optical system and an image acquisition system located on a second side of the display unit providing image capture and data capture of the operating site; and a processing system communicatively coupled to the image acquisition system and the image display providing the magnified and augmented live stereo view to the image display based on the image capture and the data capture of the operating site from the optical system and the image acquisition system.

In yet another exemplary embodiment, a method using a digital stereo microscope includes positioning and adjusting a display unit above an operating site; enabling the display unit, wherein the display unit comprises an optical system and an image acquisition system located on a side of the display unit adjacent to the operating site, and wherein the display unit comprises an image display on a side of the display unit opposite to the side facing the operating site; providing image capture and data capture of the area of interest via the optical system and the image acquisition system; processing the image capture and the data capture via a processing system; positioning a user's hands and/or tools in the operating site while maintaining the user's eyes having a view in a collocated manner looking at the image display; and presenting a magnified and augmented live stereo view of the operating site via the image display based on the processed image capture and the processed data capture of the area of interest from the optical system and the image acquisition system.

BRIEF DESCRIPTION OF THE DRAWING(S)

Figure 3:
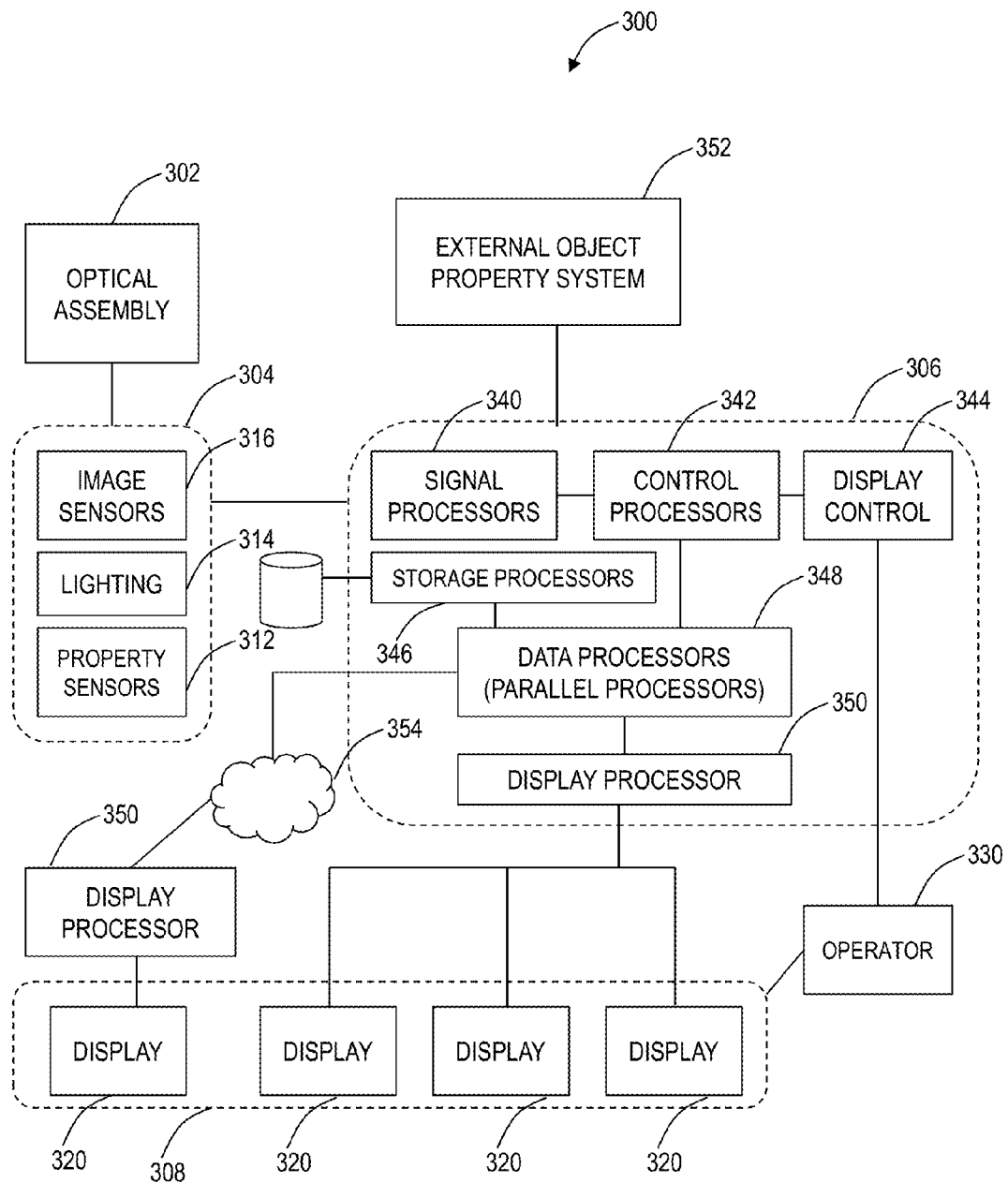
Figure 4A:
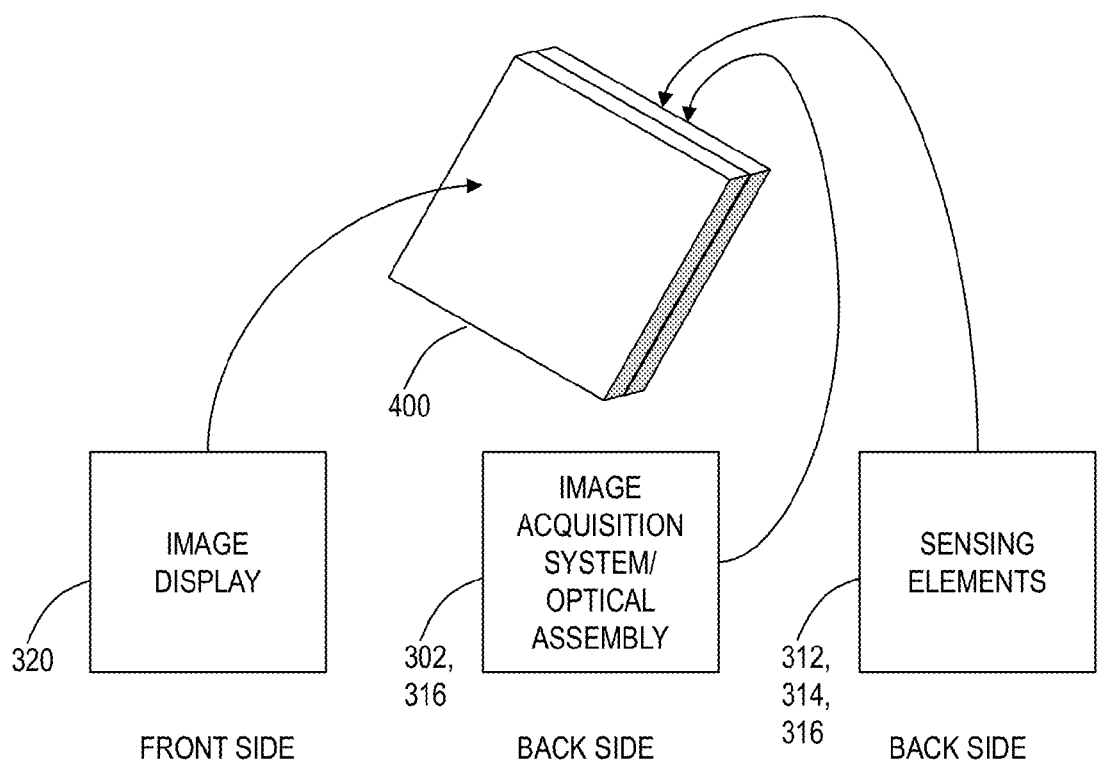
Figure 4B:
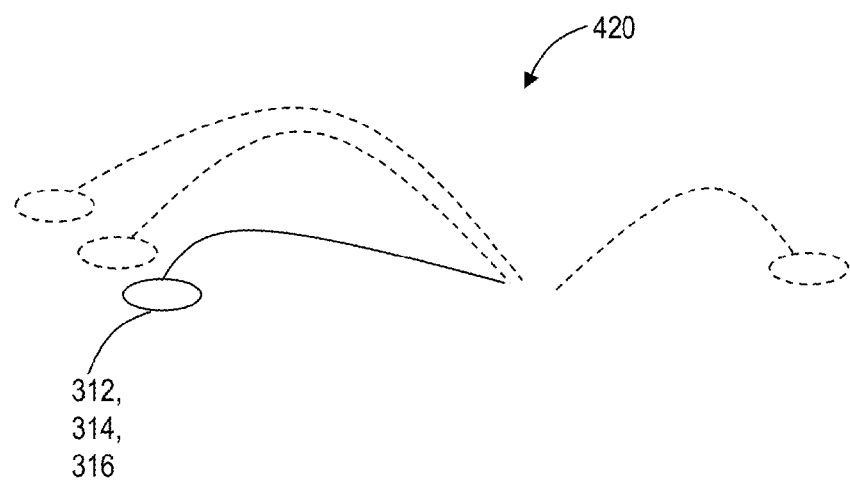
Figure 5A:
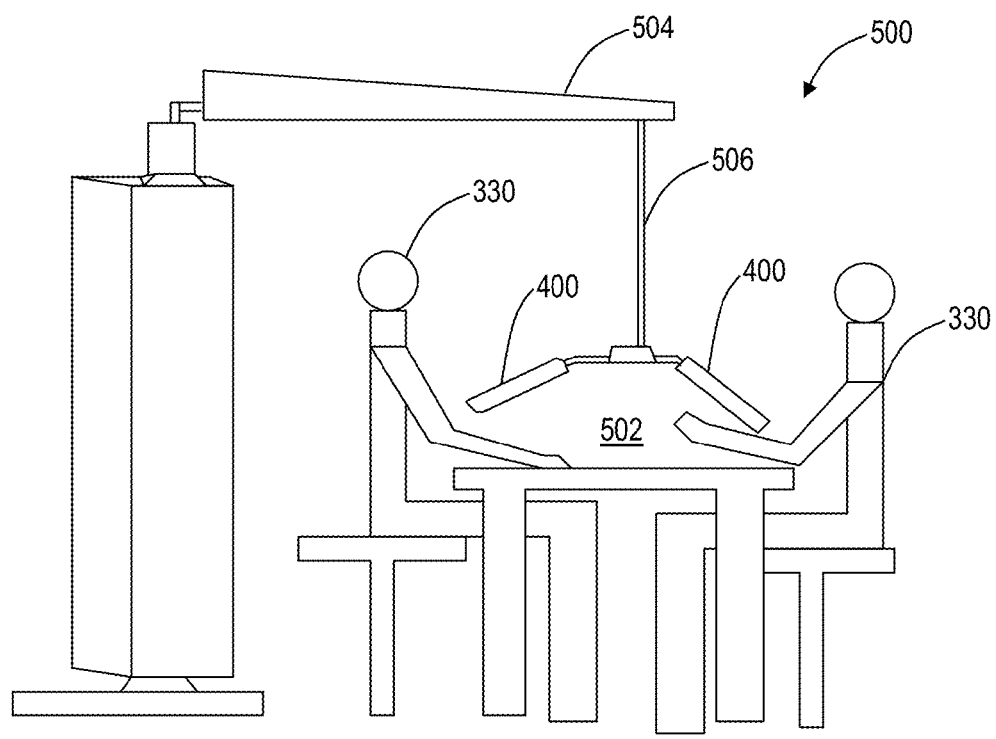
Figure 5B:
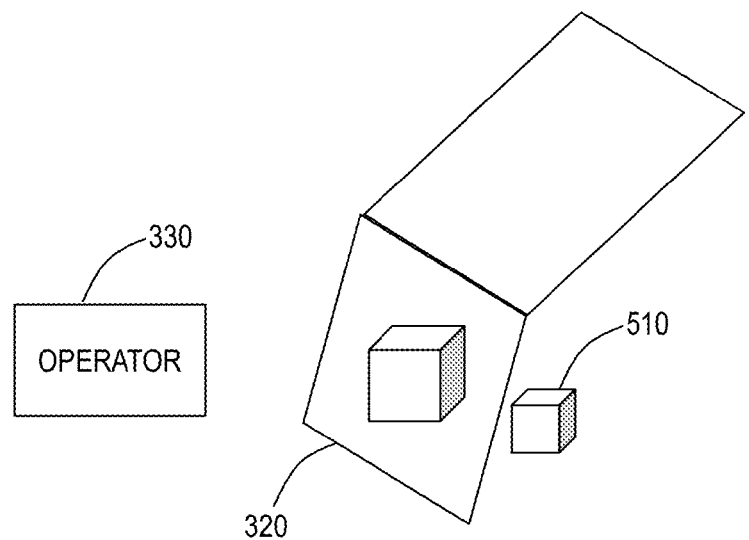
Figure 6:
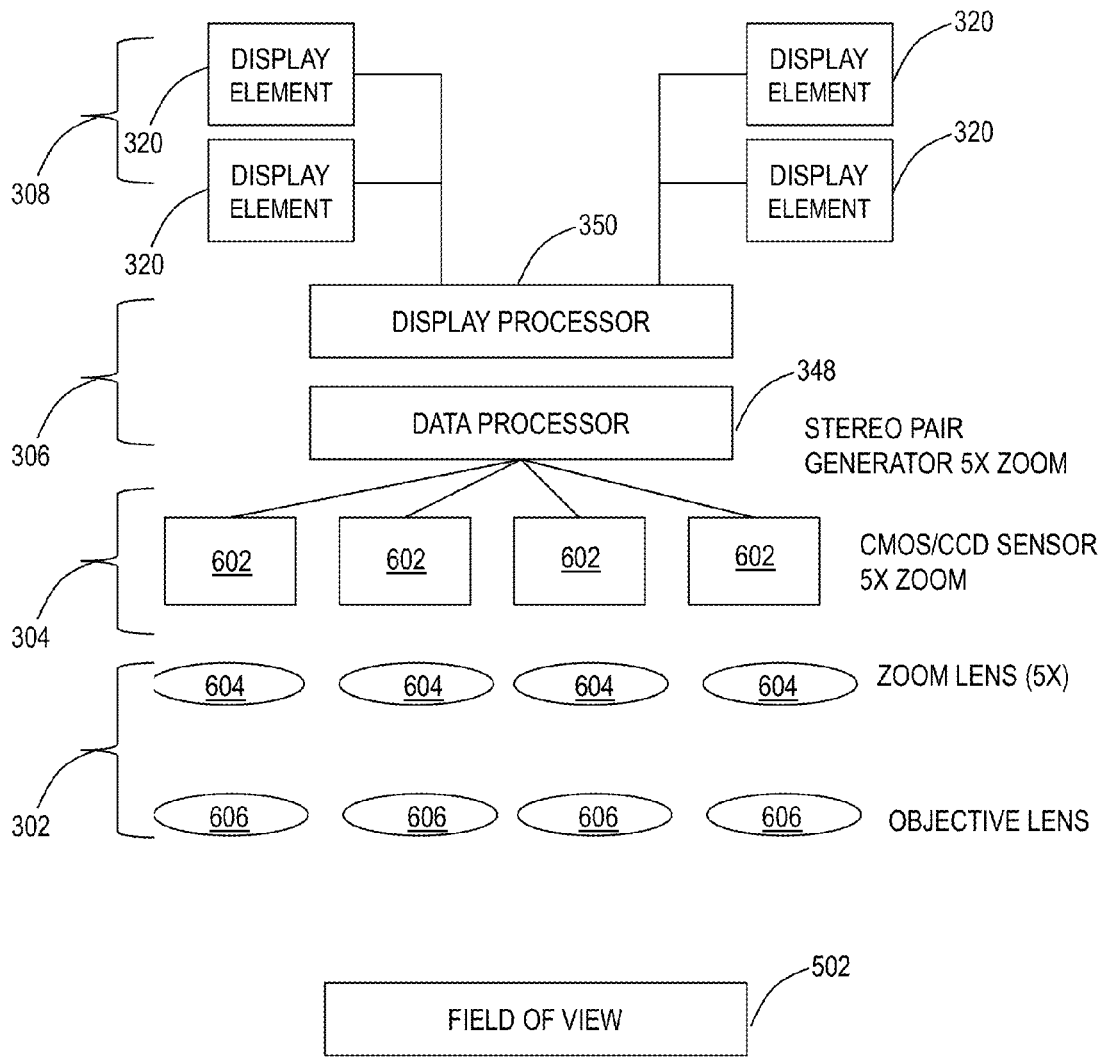
Figure 7:
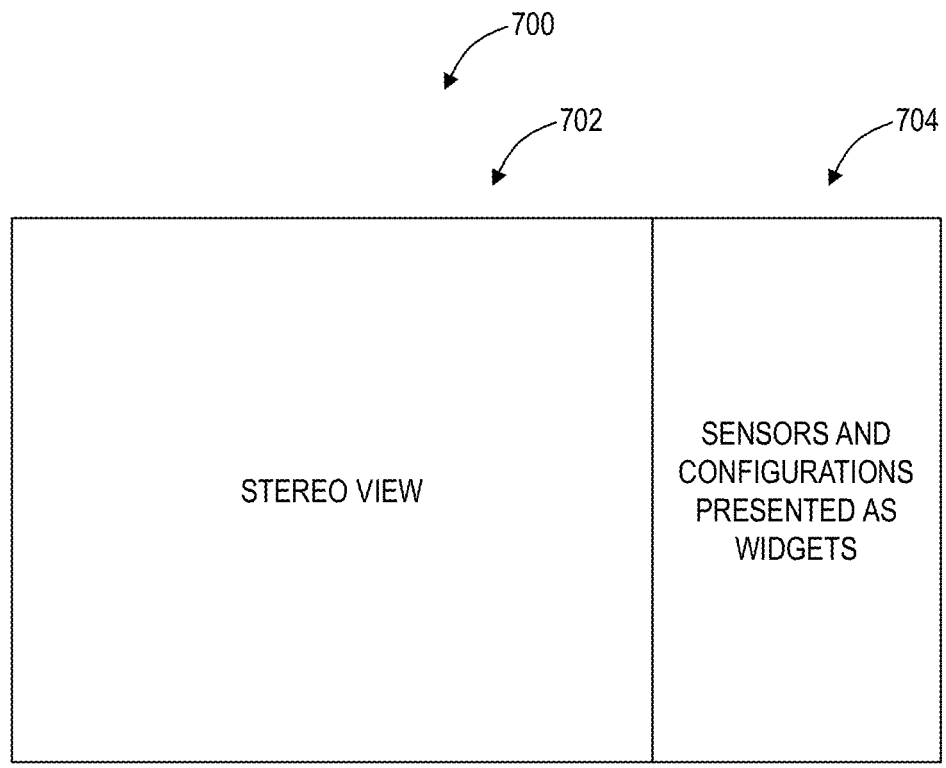

Exemplary and non-limiting embodiments of the present disclosure are illustrated and described herein with reference to various drawings, in which like reference numbers denote like method steps and/or system components, respectively, and in which:

FIG. 1 describes a prior art SLM/DSM system with optional digital adaptation by replacing the oculars by a pair of image sensors and stereoscopic display;

FIG. 2 describes the prior art relationship between distance to the object, focal length of the lens, separation of lenses and the disparity of the image pixels in the left and right eye views in a stereoscopic view;

FIG. 3 describes a digital stereo microscope with image augmentation capabilities according to an exemplary embodiment;

FIG. 4A describes one preferred arrangement of image sensors in the back-side of the display unit according to an exemplary embodiment;

FIG. 4B describes another preferred arrangement of image sensors on a flexible arm fixed to a stand according to an exemplary embodiment;

FIGS. 5A-5B describes a hand-eye collocated stereo display with FIG. 5A FIG. 5. a describing a schematic of the system with two users sharing a display and FIG. 5B describing the display arrangement and indirect viewing according to an exemplary embodiment;

FIG. 6 describes a multi-camera system achieving high magnification and high resolution using an optical lens assembly, an image sensor, a display frame processor and a flat panel display according to an exemplary embodiment; and FIG. 7 describes the user interface for configuring the digital microscope.

DETAILED DESCRIPTION OF THE INVENTION

In various exemplary embodiments, surgical stereo vision systems and methods for microsurgery enable hand-eye collocation, high resolution, and a large field of view. Multiple multimodality sensors, including image sensors, capture properties of an object under the view of the system and the user's micro manipulations of the object. The captured live view is augmented with data from sensors and external databases to aid real-time micro manipulation of the object. The system provides multiple views on one or more flat-panel stereoscopic displays, collaborative manipulation of the object, real time measurements, and panning and tilting of the field of view without moving the object. The system supports microsurgical manipulations to be performed on a patient by a group of surgeons and imparts training to surgeons by recording and replaying the surgical manipulations with a phantom object in the field of view. The system includes a DSM that provides augmented and collocated live stereo views to rectify the limitations of conventional systems. The system uses optical elements and imaging sensors for image capture, digital computing for processing, and digital displays for stereoscopic viewing. In addition to the optical imaging, the system includes multimodality sensors and different image augmentation schemes for improving the visualization of and interaction with the operated site.

An objective of the surgical stereo vision systems and methods is to achieve SLM parity in resolution and magnification used in surgery. This includes achieving continuous zoom using a movable intermediate lens assembly between the objective lens and ocular without the use of intermediate lens assembly.

Another objective includes a reduction in viewing latency to be unnoticeable to the human eye. Due to the indirect viewing of the real scene, latency introduced between what happens at an operating site and what is seen in the video of the live interaction which may disrupt the surgical procedure.

Yet another objective is to provide better functionality than conventional SLMs and DSMs by providing scene augmentation and alternate views. Multimodality sensors and image sensors on flexible arm can be used to provide augmentation and alternate views. The video streams are stored and replayed to allow surgical training in the same environment as that of the actual surgery.

Another objective of the surgical stereo vision systems and methods is to provide better ergonomics of stereo interaction for long surgeries through a hand-eye collocated stereoscopic display with support for pan, variable zoom, and tilt of the field-of-view. Advantageously, a stereoscopic view will not be lost by moving the head. Still yet another objective is to allow collaboration in the surgery having multiple surgeons and surgery assistants to simultaneously share the live view and multiple surgeons to cooperate sequentially without causing stereopsis related delays.

Referring to FIG. 3, in an exemplary embodiment, a block diagram illustrates a digital stereo microscope system 300. The digital stereo microscope system 300 includes an optical system 302, an image acquisition system 304, a processing system 306, and an image display system 308. The image acquisition system 304 includes a collection of object property sensors 312, a collection of lighting resources 314, and a collection of image sensors 316, in data communication with the image display system 308 via the processing system 306 and connected to the optical system 302 through the image acquisition system 304. The optical system 302 captures the field of view and sends an optical image to the image sensors 316 for generation of high resolution digital image of the scene. The image sensors 316 can include, without limitation, CMOS, CCD, photo-voltaic sensors, infra-red sensing elements, and the like.

The image processing sub-system 320 includes signal data processors 321, control data processors 322 and image data processors 325. The human operator 350 places the display units 341 and sensing elements 313 to yield a stereo view of the operating site using the display control 323. The lighting resources 314 are configured to provide variable amounts of visible light to the field of view. The object property sensors 312 are used to provide data to the processing system 306. The object property sensors 312 can include, without limitation, infra-red transceivers, ultra-sound transceivers, laser transceivers, light field cameras, depth sensing cameras, and the like.

Referring to FIGS. 4A-4B, in exemplary embodiments, a diagram illustrates a display/image sensor unit 400. In particular in FIG. 4A, components of the optical assembly 302 and the image acquisition system 304 can be disposed on a back side of the unit 400 with a display unit 320 on the front side of the unit 400. Further, each of the various sensing elements 312, 314 can be independently or collectively controlled by a human operator 330. As is described herein, the design of the display/image sensor unit 400 is critical to enabling hand-eye collocation as the display 320 is placed over an object of interest while hands of the human operator 330 manipulate the object of interest. The sensing elements 312, 314 may either emit sensing rays such as visible light, ultrasound or infra-red, collect sensing rays, or both emit and collect sensing rays.

Some of the sensing elements 312, 314 may be placed on a flexible arm 420 as shown in FIG. 4B and brought to an operating site. The operating site includes the field of view of the system 300 and outside the field of view of the system 300. Some of the sensing elements 312, 314 such as the visible light camera and infra-red camera may be placed on both the flexible arm 420 and the back side of the display unit 400. The arrangement of camera elements and other sensors may be along a curve. The arrangements can also be along a line or along a curved surface, so as to aid increasing the field of view. The position and orientation of one or more sensing elements may be controlled by the human operator. Also, the image sensors 316, the light sources 314, and/or the object property sensors 312 can be arranged on one of the flexible arms 420 which can be moved to focus to the operating site with manual assistance. These additional sensing elements on the flexible arms 420 are used to obtain views that are not possible with zooming and panning of the current field of view. For example, the self-occluding portion of a tissue can be made visible only through an alternate angle of view. It requires either moving the patient or tilting the image sensors 316 fixed on the back-side of the unit 400. By tilting the camera, the current view of the operating site is lost, i.e. hand-eye collocation is lost with the unit 400. By having the additional image sensors 316 fixed to the flexible arms 420, alternate views can be composed within the current viewing context. Alternate views can also be obtained from the plurality of image sensors 316 arranged at the back of the display. The limited view of the DSM and SLM systems are overcome through this arrangement.

Referring to FIGS. 5A-5B, in exemplary embodiments, diagrams illustrate use of the unit in a surgery system 500 with a hand-eye collocated stereo display. FIG. 5A shows a schematic of the system 500 with two users sharing the system 500 and FIG. 5B shows the display arrangement and indirect viewing of the display unit 400. Specifically, a human operator 330 initially places the display unit 400 along with the mounted sensing elements above an operating site 502 to view the operating site 502. An anatomical view of the operating site 502 is projected onto the display unit 400 and the human operator 330 can give control commands to zoom, pan, focus, etc. The operating site 502 can be an area of interest over which the display unit 400 is located and which is magnified in the display 320 of the display unit 400.

The processing system 306 generates commands to orient one or more of the sensing elements 312, 314, 316 in response to the human operator's 330 commands. The human operator 330 may adjust the height and viewing angle of the display unit 400 without invoking the processing system 306. For example, the system 500 can include an articulated arm 504 and a display mounting system 506 that allow adjusting the position of the display 400 at convenient viewing height and angle as well as leaving sufficient working distance. Based on the human operator's 330 viewing and working distance configuration, and the indication of the operating site 502, the selection of elements 312, 314, 316 and its orientation is decided by the processing system 306.

The location of the operating site 502 may be indicated by projecting a cursor 510 onto the scene. The human operator 330 moves the cursor to the desired site. The location of the operating site 502 may also be indicated by the human operator 330 by entering the anatomical location of the operating site 502 and then perform operations of pan, tilt and zoom to select the view and desired magnification. The human operator 330 performs the pan, tilt and zoom using one or more of the following methods. The human operator 330 may use a control knob or knobs associated with the unit 400 to increase and decrease each of these parameters. The human operator 330 may use a virtual object projected on the scene to control the parameters. Multiple methods are provided for convenience and safety. The human operator 330 may adjust the disparity and the distance between the eye and the display 320 to obtain the stereo view. These finer adjustments are done using the tool tip or using the control widgets.

The system 300, 500 may be operated in three modes, the pre-operative mode where manual control as well as control knobs is used to position the system 300, 500. During the surgical operation mode, the fine controls are done using the virtual objects such as the virtual cursor, and control widgets projected onto the field of view. In the post-operative mode, a greater field of view is provided to track the tools returning to the tool chests.

The image sensors 316 can include various cameras which can be positioned in various locations in the system 300, the display unit 400, and the surgery system 500. In an exemplary embodiment, the surgical vision systems and methods operate with the various cameras each acquiring images of an area of interest at a maximum magnification and the associated reduction in magnification being done in software via the processing system 306. Of course, the surgical vision systems and methods can also rely on lens associated with the various cameras. In an exemplary embodiment, some of the cameras are fixed on the back side of the display unit 400. In another exemplary embodiment, some of the cameras are configured to move, pan, tilt, etc. In yet another exemplary embodiment, some of the cameras are mounted in different locations in the surgery system 500 from the display unit, e.g. ceiling, walls, etc. In yet another exemplary embodiment, some of the cameras are movably attached to the flexible arms 420. In still yet another exemplary embodiment, some of the cameras can be in a linear or curved camera array. Of course, combinations are contemplated of the foregoing. In the various exemplary embodiments, camera position is such that a view can be obtained of the area of interest with the operator's 330 hands and/or tools in between the display unit 400 and the area of interest, i.e. the operating site 502. Importantly, the cameras are all communicatively coupled to the processing system 306 for presenting live streams which can be manipulated by the processing system 306 for display to many different users simultaneously including different views to different users simultaneously. The cameras can be collectively positioned such that the human operator 330 can maintain hand-eye collocation with the operating site.

Referring back to FIG. 3, in an exemplary embodiment, the system 300 uses two cameras (i.e., image sensors 316) mounted on the back of the display unit 400, a camera (i.e., an image sensor 316) mounted on the flexible arm 420, a processing unit collectively referred to as the processing system 306, and two display units 400 connected to the processing system 306. The processing system 306 can have several hundred processors for processing the camera generated live stream. Specifically, the processing system 306 is configured to receive data from the image acquisition system 304 and generate stereoscopic views on the image display system 308 for hand-eye collocation at the operating site 502. Stereoscopic views include one exemplary presentation on the image display system 308. Others are also contemplated for providing depth perception. While presenting stereoscopic views, the human operator 330 can use glasses for viewing the image display system 308. An exemplary description of a system using shutter glasses is described in U.S. Patent Publication No. 2010/0103247, co-invented by the inventor of the present application, published Apr. 29, 2010, and entitled "AN IMAGING DEVICE AND METHOD. Since this priorart system uses camera configuration to generate stereo pairs, it has same physical limitations as that of the optical microscope that the field-of-view, depth-of-field and magnification are interrelated. The prior-art system gets 2 cm to 8 cm work space which is insufficient to perform surgical manipulations. The present invention eliminates those limitations.

The processing system 306 can include various processors such as signal processors 340, control processors 342, display control 344, storage processors 346, data processors 348, and display processors 350. Variously, the processing system 306 is configured to process configuration and control commands, perform storage and retrieval of object properties such as via an external object property system 352 as well as for processing the object property sensor data from the property sensors 312. The signal processors 340 communicate and control the image acquisition system 304. The control processors 342 communicate and interface with the display control 344 which communicates and interfaces with the human operator 330.

In an exemplary embodiment, the control processors 342, the display control 344, the signal processors 340, and the storage processors 346 resides in a host central processor unit or units (CPU) and the data processors 348 resides in a large number of processors attached to the CPU through an interface, i.e. a bus such as Peripheral Component Interconnect Express (PCIe). The communication between host CPU and the PCIe hosted processors can be very infrequent. In configurations where a light projector for the lighting 314 is used to augment the display 329, the host CPU provides the display signal to the projector. The system 300 can also include multiple display processors 350 connected to the data processors 348 either via the interface or a network 354 connection. The display processors 350 are also communicatively coupled to the display 320.

For initial configuration, the system 300 is powered on and the display units 400 are moved to the site of the surgery. Once stereo views are visible in the display 320, the human operator 330 picks sensors from the set of sensors presented on the display 320 and places them in the three dimensional (3D) space. When sensors are connected, the data will be displayed at those positions. Once the human operator 330 view operations are completed, the sensor icons are removed from the display 320 by user interaction.

Once the first display unit 320 is calibrated to convenience, the second display unit 320 is calibrated by another respective user to suit the view parameters. The disparity for the stereo pairs may be different for the second user; however, the camera movements are now arrested. The user operation results in building disparity computation matrix that affects only the processing of the stereo pairs. The relative camera movements suggested by the second user is factored into a processing vector which is applied to the incoming viewing pairs. When both camera units are calibrated, further fine tuning of the calibrations is possible with both display adjustments results in changes in a transformation vector. This can be repeated for additional users.

Multiple surgeons and assistants may calibrate the system to their visual comfort and store the calibration against their named icons. Then during the surgery, the respective surgeon can bring the calibration by touching and activating their stored configuration parameters. Surgeons could also be recognized by the system through biometric recognition. The transformation vector may be either stored in the local display processor 350 or in the processors 348). When the transformation vector is stored in the local display processor 350, the processors 348 fuse the information that need to be processed by the human visual system. Since the various cameras associated with the system 300, the unit 400, and the system 500 are all capturing portions of the area of interest, the processing system 306 can be used to synthesize different live views simultaneously for different displays 320. For each view the operator may choose to see the same as what the other operator is viewing or an independent view (through another set of camera) or a combination of the views on the same screen. Generally, the system 300, 500 is configured via the various components contained therein to capture a whole area from an image perspective and to synthesize each person's view on the fly via the processing system 306.

With respect to hand-eye collocation, the human operator 330 performing a surgery at the operating site 502 will see the display 320 as if the display 320 was a magnifying transparent glass without the limitations of a magnifying glass. In a basic case of no magnification, it would be like looking through a glass. Of course, the display unit 320 contemplates magnification and augmentation of the magnifying glass. However, the systems and methods described herein are not limited to a collocated view. The operator 330 can choose to view an area of interest that would not be visible if he were to look through the glass model, for example the side of the work area facing away from the operator. The system 300, 500 could have cameras arranged in such a way to image those and make them available to the operator without tilting the scope or the subject. This is a huge advantage in surgery. Even with the direct collocated view, there will always be occlusion due to the operator hand and tools hiding the work area. Once again cameras can be placed (multiple statically placed cameras on a plane or a curved surface or few cameras that are moved electronically using motors) such that the occlusion can be minimized.

Composing the signal information from the image acquisition system 304 with the live stream displayed on the display system 308 involves a two-step process. In a first step, the information is streamed into the processing system 306 including device memory and processors that are responsible for the portion of live stream data indexes the signal information and fuse them into the common display. A second step includes performing various processing techniques bon the information by the processing system 306 prior to sending the processed information to the display 320.

The system 300 can be controlled by contact and non-contact means. Tool tip position and gesture are used to enter into command mode. For example, during a surgery, surgeon needs to change the magnification or select an opposite view. Surgeon can move the tooltip to a plastic reference object placed in the field of view of the microscope and having a specific pattern and touches it. This switches the system 300 to command mode and brings up virtual widgets which can then be chosen based on gestures. Magnification of widget overlay is controlled by up/down movements of the tooltip in command mode. Similarly, for camera selection, the widget brings up a palette of cameras and user selects them by movement. The tooltip and the virtual object must be easily recognized from video stream and should be prioritized in the data processing.

Another control operation is that a user annotates an object in the visual field using a tool tip for sharing information for future use to aid a collaborating user. The annotation may also may be an instruction to the collaborating user and used immediately. For example, an operator is able to measure angles and distances in the visual field between identified points and identified lines.

In another control operation, the user may pan or tilt the field of view or zoom a selected sub-field of the field of view. For example, a surgeon may want to see a portion of the current operating site occluded by a tissue. An alternate view can be requested without moving the patient. In another example, the surgeon may mark a portion of the tissue in the command mode and request it to be zoomed. The zoomed portion may be displayed as an overlaid or as a separate a picture in a designated portion of the screen.

The system 300 contemplates various methods for command input by the human operator 330, such as hand interaction, foot pedals, etc. Also, gestures are contemplated in the area of interest, i.e. by the operator's 330 hand or tools. For example, the operator 330 can use ordinary surgical tools for issuing commands to the system 300 in addition to the foot pedal based control or the like. This could be done by say first touching a special unique object in the field of view and thereafter using tool gestures. The operator 330 returns to normal mode by once again touching the special object.

In an exemplary embodiment, the display 320 can provide a high definition stereoscopic display of the field of view, and can include a 1920×1080 pixel stereoscopic display. The display 320 can also display additional special elements. For example, the display 320 may show control widgets in a designated portion of the display 320 and movements in this portion of the display is treated as commands. The display 320 may also contain object properties as detected by the property sensors 312. For example, the temperature at an operating site may be displayed in a separate area. It may also be displayed as an overlay.

The display 320 of one user may be different from the display 320 of another user. For example, a user may choose to perform pan, tilt and zoom and see a different display than the collaborator in a special display mode. In the normal display mode, all views are shared.

In an exemplary embodiment, the zoom levels available in the system 300 are from 6× to 12× though only a magnification of up to 5× is used commonly in surgery due to the dexterity limits of human hand. Higher magnifications are useful for robot guided surgery or other applications. The system 300 contemplates use in manual surgery, and manual surgery with tremor reducing devices which limit the operable magnifications.

Another type of magnification occurs when the system 300 uses a Complementary metal-oxide-semiconductor (CMOS)/charge-coupled device (CCD) sensor. The CMOS/CCD sensor can be 5 cm×5 cm in dimension with 1920×1080 pixel read out for display on a 22 inch screen of 1920×1080 pixels. The scale factor is of the order of 5 without using optical zoom. In addition, optical zoom may be employed to increase the magnification of selected tissue sections for surgeon's view.

The system 300 overcomes many data processing and transmission challenges in conventional systems. For example, the system 300 constructs a stereo view and let the human visual system compose a 3D object through stereopsis. A very high resolution of the live image stream is necessary for faithful reproduction of the 3D object in fine details. Especially, in microsurgery, where surgical manipulations are done on a highly magnified object, the distortions are minimized to gain fine details of the operating site 502. The resolution requirement increases with the magnification required. For a magnification of 3×, the high definition (HD) resolution (1920×1080 with 24 bits deep) is the minimum required. The number of frames from the camera sensors can be at 30 frames/sec, giving rise to 30×1920×1080×3 bytes, which is approximately 178 MB~200 MB per second per sensor. With an average of four camera sensors active at the same time, 800 MB/sec bandwidth is necessary. The high bandwidth requirement causes many challenges. The number of memory transfers that are permitted in a frame operation must be limited to avoid causing delays.

For example, if the memory bus is 512 bits wide and memory clock is 1017 MHz and are using double data rate RAM, then the peak theoretical memory throughput is 1017× 106×512×2/(8×10243)~130 GB/sec. The theoretical transfer rate is not achieved, because it assumes a single memory transaction with negligible setup and terminates costs. It only serves as a guide. In practice different elements of the memory segments are accessed and based on the access pattern, the number of memory transactions needed is much higher. Hence algorithms that process to produce stereo pairs are used to have aligned memory access for the device to reduce the number of memory transactions.

Another problem is the computation needed to perform operations on the stereo pairs. Stereo pairs are produced by two cameras, each of focal length f, fixed on a baseline with a baseline distance B apart and collects incident light on an object placed at a distance D. The two cameras will produce the image pixel which differs by a distance d for the point object.

$$D = \frac{Bf}{d} \quad (1)$$

The point object produced two image points, one for the left image and another for the right image. Their difference in their position in the image is an indication of the relative depth of the object. Finding the corresponding points in each of the images and thereby finding the disparity or the relative horizontal shift is essentially the stereo computation problem. The problem is solved by finding the pixel with least difference in intensity. This is an extensive computation requiring large CPU resources and high memory bandwidth.

Typically, find the SSD (sum of squared differences) between the right and left image intensities to identify the pixel correspondence in the pixel arrays L and R corresponding to the left and right images. For each pixel, the minimum SSD value indicates a candidate correspondence pair. The computation is nearly impractical to be done at live streams at high resolutions such as HD resolution.

$$SSD_{x,y} = \Sigma_{i=x+w}^{x+w} \Sigma_{j=y-h}^{y+h}(L[i,j]-R[i-k,j])^2 \quad (2)$$

If the pixels are to be corresponded, then the stereo images must be searched for sum-of squared distances. In addition, differences in the focal length of the two cameras, the lighting, can all contribute to ambiguity in determining correspondence in the image plane. For live streaming of stereo, the difficulty is in performing the processing in real time. The present system 300 uses selective processing of regions to avoid delay. The regions that need to be updated more frequently are processed by more number of processors in the processing system 306. Specifically, the selective processing can include uniquely patterned objects in the subject area (e.g., patterned clothes, reference frames, tools, etc.) to help match the two views. That is, the system 300 can make use of the constraints associated with the operating site 503 for additional information that can be used to make fast— uniquely patterned objects in the subject area to help match the two views.

Also, the system 300 can include techniques that inflate the depth perception on a gradient with a focus point as its centre. The idea is to have greater clarity at the focal area and gradually decreasing clarity at areas further away from focus. This allows for speed and processing efficiency while focusing where it is important, the focal area of the operating site 502.

The system 300 offers special operations such as removing occlusion of the tissue due to bleeding by selecting the IR camera sensor elements and processes the streams originating from both IR and visible light sensing elements.

As described herein, the processing system 306 can be divided into five data processing modules, the signal data processors 340, the control data processors 342, the image data processor 348, the storage processors 346, and the display processors 350. The display control 344 module is also part of the processing system 306. The signal data processors 340 receive, via the elements 312, 314*m*, non-image sensing elements of the digital microscope as well as vital signals from other sensing elements that are not part of the digital stereo microscope. The received signals may indicate the current temperature of the operating site or pressure, pulse rate, ECG etc. These are monitored by functional specialists and the surgeon may be informed. When such information needs surgeon's attention, it can be brought to surgeons view by projecting the information into operating view of the surgeon and away from the operating site.

Information such as signal data, measurement data, and control widgets may be projected into the operating site by combining the images by the image processor into a single stereo pair of images send to the display unit. Alternatively, such information may be projected by a tiny projector mounted on the back side of the display and the combined image stream may be processed by the image data processor.

The system 300 can fuse a selected sensor stream of surgical motion and fuse it with the image of the surgical site to simulate conditions of actual surgery by using the training surgical specimens mounted at the operating site.

In addition to the camera and lighting elements mounted on the back side of the display unit 400, a number of camera and lighting elements are provided in a spoke-and-hub arrangement, mounted on the flexible arms 420 to provide alternative views of the operating site 502. The image data processor 348 combines these newly presented views with the views from the camera elements mounted on the back-side of the display units 400 to provide views from a different angle.

The operating surgeon is able to perform virtual tilting of the patient using the views of the images produced by the spoke-and-hub camera system. The surgeon virtually tilt or roll the patient by using a virtual control widget which results in combining the views from multiple of the spoke-and-hub camera system.

The image data processor 348 is able to compose sets of image stereo pairs using multiple image views from the sensing elements both from the display mounted sensing elements and from the spoke and hub sensing elements. The display unit 320 is optionally able to perform adjustments to the received stereo pairs when all display units are receiving same stereo pairs.

Registration and calibration of the system 300 can be performed before the surgery by using a phantom object to establish the relationship between multiple sensor elements are their current positions. It may also be achieved with a real object or a marker placed in the field of view. Along with position of the imaging, property sensing elements, the correspondence between the object coordinates and image coordinates is achieved through registration of a fixed marker in the field of view of the microscope.

The live video data, signal processing data, object property data, and collaborating user's input are to be combined into the same virtual space and presented in the stereoscopic display 320. There are different processing steps. In a first step, the video data from multiple cameras are clipped for overlapping pairs of views and corrected for matching disparity. The disparity must match the XY zoom. The combining of other data is performed in one of the following ways. In one method, a light projector projects the data into the correct locations so that the live view will have the combined data. In another method, the combining of the data is performed by the data processor 348.

The data processor 348 divides the entire data into predefined chunks. The definition of division may be based on auxiliary input signal such as motion tacking, or may be based on static division such as gradation of the visual field. Division may also divide the visual field into the operating field and command field. Some of the data are to be processed faster than the other data. For example, the command field data must be processed before the operating field. Based on the nature of the data, each chunk of data is given a collection of processors.

Referring to FIG. 6, in an exemplary embodiment, a block diagram illustrates components of the system 300 interworking with the display unit 400. The image acquisition system 304 can include CMOS/CCD sensors 602 mounted on the display unit 400. The optical assembly 302 can include zoom lenses 604 and objective lenses 606 mounted on the display unit. These components 602, 604, 606 can provide image data from the operating site 502 to the data processors 348 which performs processing to form stereoscopic views which are provided to the display processors 350 for display on the displays 320 on the display unit 400.

Referring to FIG. 7, in an exemplary embodiment, a screen diagram illustrates a screen shot 700 of the display 320 of the system 300. As described herein, the screen shot 700 can include a stereo view 702 of the operating site 502 as well as other data 704 which can include sensors and configuration data presented as widgets on the screen shot 700.

There are several advantages to the system 300. Advantages are presented for the system 300 used in performing micro-surgery though similar advantages will be present in other applications. Since the system 300 allows hand-eye-collocation, both the gaze and hand movement are coordinated and eye gaze is towards the hand movement, the surgeon's strain is reduced.

Large field of view is presented to the surgeon through the stereoscopic flat display panels that allows head movement without losing the stereoscopic view. The field of view could have a uniform resolution or a graded resolution. The large field of view takes away the need for constant zoom-in-zoom-out needed to maintain context. The stereoscopic view is immediate and does not need training.

Since the system 300 does not require intensive training to perform surgical operations by looking through a microscope and adjusting the microscope positions on the fly, it can be used in other surgeries where the surgeon is not trained in microsurgery. The system 300 improves the visibility of the operating area. An example is surgery of the eyelids practiced by cosmetic surgeons.

Another advantage is the display of critical patient information such as heart rate, which can be displayed either as direct numbers or as levels along with the same display unit or as a graph. This information may be displayed at a depth in the field of view of the surgeon, but without obstructing the view of the operating site. Other pre-surgery imagery of the operating site may also be overlaid with the live stream with correct alignment to aid in the surgery.

The live stream may be processed to provide guidance in terms of mensuration and anatomical recognition. A Surgeon is able to change the view angle without moving the patient and is able to have views from different angles at the same time. The system 300 offers a platform for integrating sensors and a method of combining the sensor information with the live video of the surgery. The hand movement of the surgeon and the live video stream of the hand movement are displayed without noticeable delay, the surgeon gets a feel of the real operating site as if the display units were not present. An expert can cooperate in the surgical procedure from a remote site with some delay in the hand movements and its video stream and provide instructions to the operating surgeon.

The remote collaboration feature also offers teaching facility wherein the expert surgeon conducting the operation can be mimicked by each of the training surgeons who have the display units with the remote stereo views being integrated with the local movements. In such applications, the display unit is able to perform simple stereo image transformations to combine the scenes by adjusting the camera positions and overlaying the received images and local video. During operation, the surgeon is able to operate the system using virtual configuration objects. This satisfies the sterile requirement of the operating environments. Surgeons can use saved configurations to bring the stereo display to their own preferred settings, when multiple surgeons time multiplex during a long duration surgery.

It will be appreciated that some exemplary embodiments described herein may include one or more generic or specialized processors ("one or more processors") such as microprocessors, digital signal processors, customized processors, and field programmable gate arrays (FPGAs) and unique stored program instructions (including both software and firmware) that control the one or more processors to implement, in conjunction with certain non-processor circuits, some, most, or all of the functions of the methods and/or systems described herein. Alternatively, some or all functions may be implemented by a state machine that has no stored program instructions, or in one or more application specific integrated circuits (ASICs), in which each function or some combinations of certain of the functions are implemented as custom logic. Of course, a combination of the aforementioned approaches may be used. Moreover, some exemplary embodiments may be implemented as a non-transitory computer-readable storage medium having computer readable code stored thereon for programming a computer, server, appliance, device, etc. each of which may include a processor to perform methods as described and claimed herein. Examples of such computer-readable storage mediums include, but are not limited to, a hard disk, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory), Flash memory, and the like. When stored in the non-transitory computer readable medium, software can include instructions executable by a processor that, in response to such execution, cause a processor or any other circuitry to perform a set of operations, steps, methods, processes, algorithms, etc.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure and are intended to be covered by the following claims.

What is claimed is:

1. A digital stereo microscope apparatus, comprising:
a display unit fixed and located over an area of interest such that a human operator places hands, tools, or a combination thereof in the area of interest and views a magnified and augmented live stereo view of the area of interest with eyes of the human operator having a view substantially collocated and in a direct field and line of view with the hands, tools, or combination thereof of the human operator in the area of interest, wherein the human operator is able perform head movement without losing the live stereo view on the display unit;
an image display located on a front side of the display unit relative to the human operator providing the magnified and augmented live stereo view;
an optical system and an image acquisition system located in part on a back side of the display unit providing image capture and data capture of the area of interest;
wherein the optical system and the image acquisition system comprises at least one objective lens and at least one image sensor; and
a processing system communicatively coupled to the image acquisition system and the image display providing the magnified and augmented live stereo view to the image display based on the image capture and the data capture of the area of interest from the optical system and the image acquisition system, wherein the optical system and the image acquisition system is configured to provide the image capture with adjustments to provide the magnified and augmented live stereo view, in real-time, performed by the processing system utilizing stereopsis.

2. The digital stereo microscope apparatus of claim 1, wherein the optical system, the image acquisition system, and the processing system provide continuous zoom without an intermediate lens assembly with the continuous zoom being performed by the processing system.

3. The digital stereo microscope apparatus of claim 1, wherein the optical system and the image acquisition system are configured to capture image data at a maximum resolution of associated hardware with augmentation, magnification, and reduction of resolution of the image data being performed by the processing system.

4. The digital stereo microscope apparatus of claim 1, wherein the image display comprise a stereoscopic flat display panel that allows head movement of the human operator without losing a stereoscopic view of the area of interest.

5. The digital stereo microscope apparatus of claim 1, further comprising:
at least one property sensor capturing data related to the area of interest and communicating the captured data to the processing system, wherein the processing system is configured to process the captured data and display portions of the captured data on the image display in addition to the magnified and augmented live stereo view.

6. The digital stereo microscope apparatus of claim 1, wherein the image display comprises a first image display, and further comprising:
a second image display located apart from the display unit and communicatively coupled to the processing system, wherein the second image display is associated with a second human operator, wherein the second image display comprises an independent magnified and augmented live stereo view from the magnified and augmented live stereo view of the first image display, and wherein the independent magnified and augmented live stereo view is formed by the processing system.

7. The digital stereo microscope apparatus of claim 1, further comprising:
a display control controlling the processing system responsive to the human operator for zoom, pan, and focus of the optical system and the image acquisition system via the processing system, wherein the zoom, pan, and focus is performed virtually by the processing system.

8. The digital stereo microscope apparatus of claim 7, wherein the display control is configured to track eye movements of the human operator and generate commands to configure the optical system and the image acquisition system accordingly.

9. The digital stereo microscope apparatus of claim 8, wherein the eye movement is approximated to the movement of the head and tracked.

10. The digital stereo microscope apparatus of claim 7, wherein ambient light intensity and direction of the light is controlled by the display control.

11. The digital stereo microscope apparatus of claim 7, wherein the area of interest is remote from the human operator such that hands of the human operator and eyes of the human operator are virtually collocated.

12. The digital stereo microscope apparatus of claim 1, further comprising:
cameras capturing a left eye view and a right eye view of a field of view of the area of interest, wherein the processing system is configured to time synchronize the left eye view and the right eye view for presentation on the image display; and
additional image sensing elements fixed to articulate arms for alternate views within the area of interest.

13. The digital stereo microscope apparatus of claim 12, wherein the processing system is configured to utilize a sum of squared differences algorithm to identify pixel correspondence between the cameras;
wherein the sum of squared differences algorithm selectively processes different regions of the area of interest based on which regions are updated more frequently.

14. The digital stereo microscope apparatus of claim 1, further comprising:

at least one flexible arm adjustable separately from the display unit to the area of interest, wherein the at least one flexible arm comprises at least one component of the image acquisition system.

15. The digital stereo microscope apparatus of claim 1, wherein the processing system comprises:

property data processors that produce a visual representation of a property of objects in the area of interest as a time varying graphical view or as a time varying number display for display on the image display;

control data processors that process commands from the human operator for configuration and orientation of the optical system and the image acquisition system;

storage processors that store and retrieve data in an external storage system; and display processors that produce a stereo view of the area of interest and user interaction therewith and combine with the visual representations of the property data processors and storage processors to produce an augmented stereo view.

16. The digital stereo microscope apparatus of claim 1, wherein the processing system is configured to present the magnified and augmented live stereo view with sufficient disparity between the left and right eye view images such that the human operator sees a three dimensional representation through stereopsis.

17. A surgical operating system with a digital stereo microscope, comprising:

an articulated arm comprising a display mounting system;

a display unit connected to the display mounting system;

an operating site over which the display unit is fixed and located such that a human operator places hands, tools, or a combination thereof in the operating site and views a magnified and augmented live stereo view of the operating site with eyes of the human operator having a view substantially collocated and in a direct field and line of view with the hands, tools, or a combination thereof of the human operator in the area of interest, wherein the human operator is able perform head movement without losing the live stereo view on the display unit;

an image display located on a front side of the display unit relative to the human providing the magnified and augmented live stereo view;

an optical system and an image acquisition system located on a back side of the display unit providing image capture and data capture of the operating site; and a processing system communicatively coupled to the image acquisition system and the image display providing the magnified and augmented live stereo view, in real-time, to the image display utilizing stereopsis based on the image capture and the data capture of the operating site from the optical system and the image acquisition system.

18. The surgical operating system of claim 17, wherein the optical system and the image acquisition system comprises at least one objective lens, at least one zoom lens, and at least one image sensor, and wherein the optical system and the image acquisition system provide continuous zoom without an intermediate lens assembly;

wherein the image display comprise a stereoscopic flat display panel that allows head movement of the human operator without losing a stereoscopic view of the area of interest.

19. A method using a digital stereo microscope, comprising:

positioning and adjusting a display unit above an operating site to a fixed position;

enabling the display unit, wherein the display unit comprises an optical system and an image acquisition system located on a back side of the display unit adjacent to the operating site, and wherein the display unit comprises an image display on a front side of the display unit opposite to the operating site;

providing image capture and data capture of the area of interest via the optical system and the image acquisition system;

processing the image capture and the data capture via a processing system;

positioning a user's hands, tools, or a combination thereof in the operating site while maintaining the user's eyes having a view in a collocated manner and in a direct field and line of view looking at the image display, wherein the front side and the back side are relative to the user; and presenting a magnified and augmented live stereo view of the operating site, in real-time, via the image display utilizing stereopsis based on the processed image capture and the processed data capture of the area of interest from the optical system and the image acquisition system, wherein the human operator is able perform head movement without losing the live stereo view on the display unit.

* * * * *